United States Patent [19]

Berry

[11] Patent Number: 4,775,370
[45] Date of Patent: Oct. 4, 1988

[54] MIDDLE EAR DRUM VENTILATION AND DRAINAGE TECHNIQUE

[76] Inventor: Yale J. Berry, 134 Clinton Rd., Brookline, Mass.

[21] Appl. No.: 135,537

[22] Filed: Dec. 18, 1987

Related U.S. Application Data

[63] Continuation of Ser. No. 862,719, May 13, 1986, abandoned.

[51] Int. Cl.[4] ............................................. A61M 27/00
[52] U.S. Cl. ..................................................... 604/264
[58] Field of Search ................... 623/12; 604/264, 26; 128/329 R, 151–152

[56] References Cited

U.S. PATENT DOCUMENTS 4,650,488  3/1987  Bays et al. ..................... 604/264
4,695,275  9/1987  Bruce et al. .................... 604/264

Primary Examiner—John D. Yasko
Assistant Examiner—Gene B. Kartchner
Attorney, Agent, or Firm—Rines and Rines; Shapiro and Shapiro

[57] ABSTRACT

A ventilation and drainage tube for a child's ear drum having a preferably tapered lumen increasing toward the ear canal side of the tube for relieving middle ear pus and other pressure build-up and automatically washing out crusts and other plugging materials.

5 Claims, 1 Drawing Sheet

MIDDLE EAR DRUM VENTILATION AND DRAINAGE TECHNIQUE

This is a continuation application of Ser. No. 862,719 filed May 13, 1986, which is now abandoned.

The present invention relates to methods or techniques of middle ear drainage and to improved ventilation drainage tube structures.

To alleviate the problem of ear infections in children, ventilation tubes are customarily inserted into the tympanic membrane or ear drum which has been found dramatically to reduce the number of infections. These tubes are made of stainless steel, non wettable plastics such as Teflon, silastic, nylon and proplast materials and the like, generally having at least an inner flange so that the tube will not readily be pushed out by infection or other fluid pressures building up in the middle ear region inside the ear drum, and all being of constant or uniform diameter or lumen.

One of the problems with such tubes, however, is that these tubes themselves plug with debris, dried mucus, scale, old blood, crusts, etc. Then, with the next infection, the pressure building up behind the tympanic membrane will not only wash-out the pus developing in the ear, but also the plugged tube itself becomes dislodged since it is no longer serving as a ventilation and drainage tube. It is, therefore, necessary to perform another operation, with the disadvantages of general anesthetic, to perforate the drum and to insert another tube.

In accordance with the discovery underlying the present invention, it has been found that by modifying the lumen in the tube to provide for a greater cross-section or diameter opening in the tubular hollow on the outer or ear canal side of the tube (and preferably a divergingly tapered cross-section from the inner end of the tube to the outer end), the tubes are kept remarkably and continuously clear and unplugged, admirably solving the above-mentioned problems.

An object of the present invention, accordingly, is to provide a new and improved middle ear ventilation and drainage method or technique and tube apparatus that obviate the previously discussed disadvantages of current ventilation tubes.

Other and further objects will be explained hereinafter and are more particularly delineated in the appended claims.

In summary, from one of its aspects, the invention provides a ventilation and drainage tube for a child's ear drum having a flange at least at its inner end and an inner hollow cross-section that increases along the tube from the inner to the outer end of the tube. Preferred and best mode embodiments and details are later presented.

The invention will now be described with reference to the accompanying drawing,

FIG. 1 of which illustrates, in section, a preferred tube embodiment inserted through the ear drum;

Figure 1:
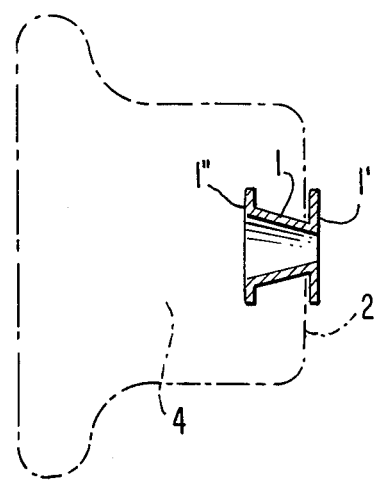
Figure 2:
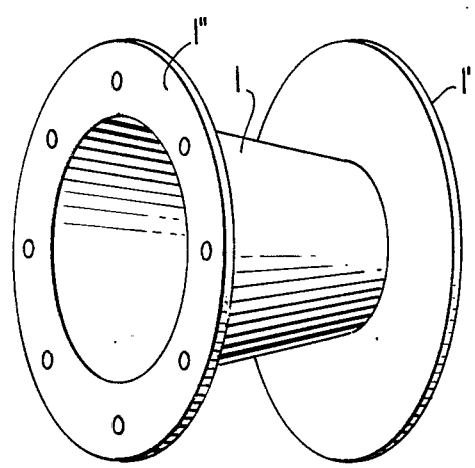
FIG. 2 is an isometric view, upon an enlarged scale, of the tube of FIG. 1.

Referring to FIG. 1, the ventilation or drainage tube is shown at 1 inserted within a perforation surgically made under anesthetic in the ear drum 2 and ventilating the inner middle ear (right-hand) side of the drum to the outer ear canal 4, for the above-described purposes. In this embodiment, the tube 1 is shown in FIGS. 1 and 2 as having an internal or inner end flange 1' and an outer preferably similar end flange 1" that tend to resist dislodging in either direction and that are interconnected (integrally formed from the same material) by the drainage tube portion 1. The outer flange 1" may be provided with circumferential apertures, as illustrated, for facilitating draining.

The lumen of the interior hollow of the tube 1, however, in accordance with the invention and unlike the before-described current and prior tubes in use, is of non-uniform diameter or cross-section, being smaller at the inner (right-hand) end and larger at the outer (left-hand), and preferably continuously divergently tapering, as shown, toward the outer ear canal side. This provides an outwardly lower impedance channel flow path such that the slightest pressure of pus in the middle ear is rapidly relieved, and any crusts or other plugging materials within the lumen of the tube (which, as before stated, is of non wettable character) have been found to be readily washed out, with the tube remaining clear and in place and operable for ventilation for much longer periods of time. A suitable variation in lumen diameter to accomplish the purposes of the invention for a tube about 1.30 mm long has been found to be from about 1.1 mm to about 2 mm.

Figure 3:
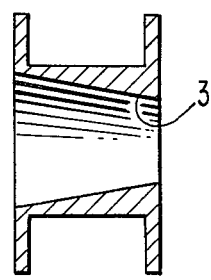
FIG. 3 is a longitudinal section, upon a smaller scale, of a current ventilation tube modified to incorporate the principles of the invention.

Present-day tbes of uniform diameter may be modified to incorporate the invention, as by tapering the thickness of the inner tube wall, as shown at 3 in FIG. 3, diverging toward the ear canal side.

Further modifications will occur to those skilled in this art and such are considered to fall within the spirit and scope of the invention as defined in the appended claims.

What is claimed is:

1. A ventilation and drainage tube for a child's middle ear drum having a flange at least at its inner end and an inner hollow cross-section that increases progressively along the tube from the inner end to the outer end of the tube.

2. A ventilation and drainage tube as claimed in claim 1 and in which the tube has flanges at both ends and is formed of non wettable surfaces.

3. A ventilation and drainage tube as claimed in claim 2 and in which said cross-section continually tapers divergingly from the inner flange to the outer flange.

4. A ventilation and drainage tube for a child's ear drum having an interior lumen that diverges progressively from the inner end to the outer end of the tube.

5. A method of improved middle ear ventilation and drainage, that comprises, perforating the ear drum, ventilating along a tubular channel through the perforation from inside the middle ear to the external ear canal, and preventing clogging of the channel by draining pus and related buildups on the inside of the drum through a lumen of said channel that diverges progressively from the middle ear side inside the drum to the ear canal side outside the drum, automatically to wash out the channel by relieving even slight pressure build-up inside the drum at the lesser lumen side of said channel.

* * * * *